United States Patent [19]
Hay

[11] 3,933,171
[45] Jan. 20, 1976

[54] ANESTHESIA BREATHING CIRCUIT WITH POSITIVE END EXPIRATORY PRESSURE VALVE

[75] Inventor: Wayne W. Hay, Madison, Wis.
[73] Assignee: Airco, Inc., Montvale, N.J.
[22] Filed: Apr. 9, 1974
[21] Appl. No.: 459,437

[52] U.S. Cl. ............. 137/493.7; 128/188; 128/202; 137/493
[51] Int. Cl.² ........................................ A61M 17/00
[58] Field of Search ............. 137/493, 493.2, 493.7, 137/493.8, 493.9; 128/142, 145.5, 145.6, 145.7, 145.8, 188, 191 R, 202, 211

[56] References Cited
UNITED STATES PATENTS

| | | | |
|---|---|---|---|
| 2,271,497 | 1/1942 | Newell | 137/493 |
| 2,841,142 | 7/1958 | Hay | 128/188 |
| 3,556,097 | 1/1971 | Wallace | 128/188 |

FOREIGN PATENTS OR APPLICATIONS

| | | | |
|---|---|---|---|
| 698,486 | 11/1940 | Germany | 137/493 |
| 149,213 | 11/1952 | Australia | 137/493.8 |

Primary Examiner—Robert G. Nilson
Attorney, Agent, or Firm—Roger M. Rathbun; Edmund W. Bopp; H. Hume Mathews

[57] ABSTRACT

A valve is provided for use in an anesthesia breathing circuit and is located between the breathing bag or ventilator and the remaining parts of the circuit. The valve comprises a housing having an inlet connectible to the bag or ventilator and an outlet which is connectible to the remaining circuit. The valve has essentially two parallel flow paths for gas; in one path there is a check valve to allow gas to pass only in a direction away from the bag or ventilator, and in the other path is located a diaphragm valve which is spring biased to a closed position and is opened at a predetermined pressure in that path. The valve allows the retention at all times of a predetermined pressure within the patient circuit and thus the operator can select the lowest pressure which the patient's lungs will reach during ventilation to insure the lungs will always be expanded to more than their normal resting state. The position and operation of the present valve also achieves its desired result without introducing appreciable resistance against the patient's exhalation.

6 Claims, 2 Drawing Figures

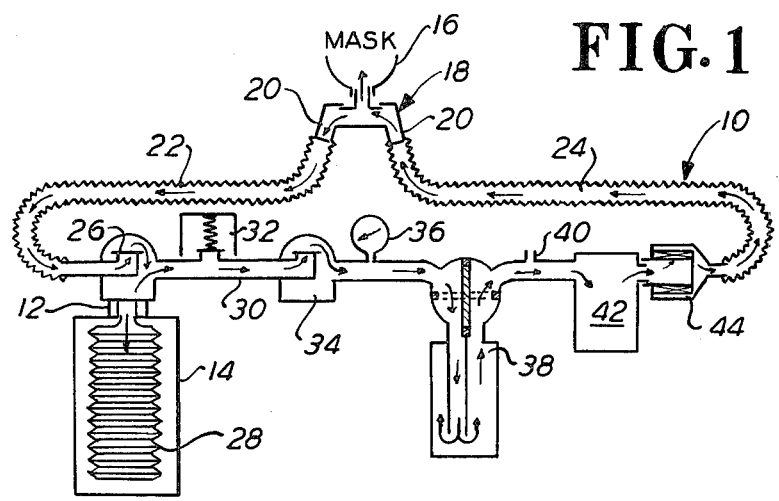
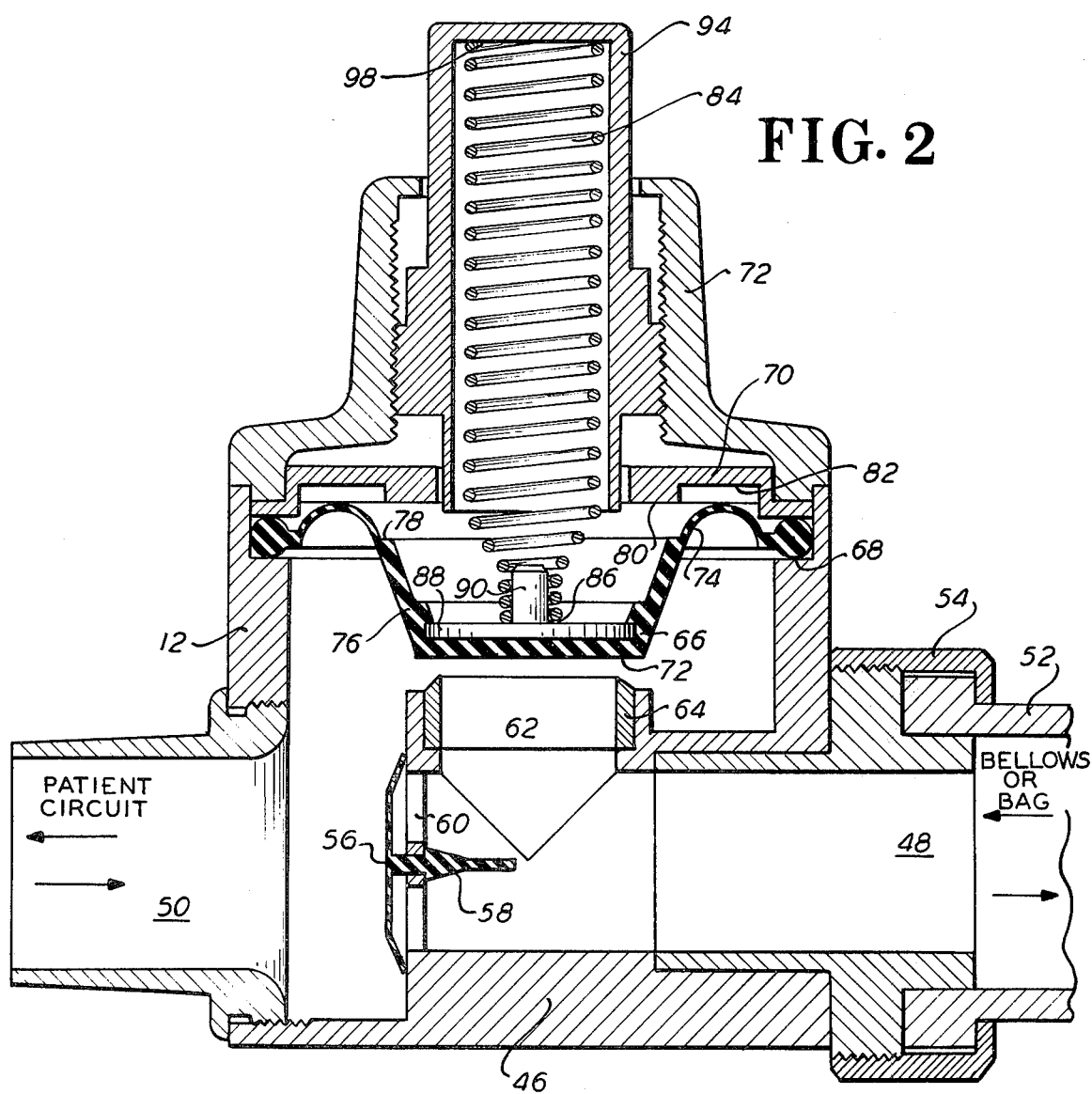

ANESTHESIA BREATHING CIRCUIT WITH POSITIVE END EXPIRATORY PRESSURE VALVE

BACKGROUND OF THE INVENTION

The present invention relates to a valve means for use with an anesthesia breathing circuit, and more particularly, to a positive-end expiratory pressure (PEEP) valve which is adapted to maintain a predetermined minimum pressure at all times within the lungs of a patient during ventilation.

It is presently known that, in some patients, a positive-end expiratory pressure is needed during ventilation in administering anesthesia or, for that matter, in maintaining a patient on a respirator. With PEEP, the patient is allowed to exhale only to a point where a positive pressure is maintained within the lungs so that at all times the lungs are maintained at or above their normal resting volume. The maintenance of such a positive pressure may prevent alveolar collapse.

Various devices are currently available which do accomplish PEEP during respiration, however, the present devices also introduce a not insignificant fixed resistance into the breathing circuit so that the patient exhales against the resistance of the PEEP device as well as the other internal resistance and pressure on the downstream side of the circuit itself. Any additional resistance in the circuit due to the PEEP device is, of course, undesirable since it tends to reduce the rate at which exhalation occurs.

In the present invention a PEEP valve is provided for placement in a patient breathing circuit between the ventilator bellows or bag and the remaining parts of the circuit. At this point in the circuit, the gas flow during respiration is bidirectional. The valve has two parallel gas flow paths; one of which includes a check valve to preclude gas from returning to the bellows or bag via that path, and the second flow path provides a diaphragm valve which opens and closes in accordance with the pressure in that flow path. The diaphragm valve is adjustable to operate at a pressure within a range of desired minimum pressures since each patient may require a different residual pressure in the lungs. By the construction of the valve, and its particular position in the circuit, minimal resistance is introduced into the patient circuit itself.

Thus, a valve is provided which allows an adjustable, accurate establishment of a PEEP in a patient circuit without also introducing a further fixed resistance which could reduce the exhalation rate of the patient.

A basic patient breathing circuit on which the present invention is an improvement, is shown by U.S. Pat. No. 3,556,097, granted Jan. 19, 1971 to D. R. Wallace for "Disposable Anesthesia-Breathing Circuit Unit" and assigned to the same assignee as the present invention.

BRIEF DESCRIPTION OF THE DRAWINGS

FIG. 1 is a schematic view of an anesthesia breathing circuit containing a PEEP valve constructed in accordance with the present invention; and FIG. 2 is a cross-sectional view of the PEEP valve as used in the circuit of FIG. 1.

DETAILED DESCRIPTION

In FIG. 1 there is shown a schematic view of an improved anesthesia breathing circuit 10 in which the valve 12 of the present invention is utilized. In the further description, the valve 12 will be explained with the use of a ventilator 14 operable to supply a pressurized gas to the patient's lungs, however, as will be later detailed, the PEEP valve of the present invention may readily be used where a squeeable bag is used to breathe the patient.

In the patient circuit 10, as shown, the normal components include a face mask 16 (or endotracheal tube) to communicate with the patient. A wye connector 18 is attached to the mask 16 and provides two tube elements 20 for connecting to a pair of conduits 22 and 24. As indicated by the arrows, conduit 22 receives the exhaled breath from the patient and connects to the ventilator 14 through a check valve assembly 26. The ventilator 14 thereby receives exhaled breath from the patient and when the bellows 28 moves upwardly, forces that gas further through the circuit 10, ultimately to the patient. The means for operating the bellows 28 is conventional, however, it is noted that the overall circuit 10 is closed when the bellows 28 within ventilator 14 is collapsing to force gas through the system. At this time the ventilator 14 is in the inhalation phase. When the bellows 28 thereafter drops, the ventilator 14 is in the exhalation phase and the exhaled breath is exiting the patient. At the end of exhalation phase the system is generally open as will be later explained.

Following through the patient circuit 10, the gas forced from bellows 28 is passed through conduit 30 inasmuch as the check valve 26 prevents the gas from being forced backwardly through conduit 22, A pressure relief valve 32 in conduit 30 is biased by a set spring pressure and opens to relieve the pressure in the circuit 10 whenever a predetermined pressure is exceeded. An exhalation check valve 34 is present in conduit 30 to maintain unidirectional flow and prevent exhalation gases from passing back through the circuit 10. A pressure gauge 36 may be included to read pressure within circuit 10. A $CO_2$ absorber 38 in conduit 30 serves to absorb the $CO_2$ from the exhalation gases and may be of conventional design employing soda-lime as the absorbent material.

An inlet 40 is provided to introduce fresh gas such as oxygen, nitrous oxide, etc. to the circuit 10. The gas flow may then pass through a vaporizer 42 where anesthetic vapors, as desired, are picked up by the gas flow for anesthetizing the patient through conduit 24. As shown, a filter 44 may also be present to remove undesirable pathogens or the like from the circulating gas.

The circuit 10 shown, indicates the location and intended functioning of the valve 12 in a typical anesthesia breathing circuit and it is understood that some of the individual components may be used in other locations in the anesthesia circuit, or one or more eliminated completely. In any anesthesia circuit, however, the location of the PEEP valve 12 of this invention is important since it must be positioned between the ventilator 14 (or breathing bag) and the remaining system. At this particular location, the gas flow is bidirectional while throughout the rest of the anesthesia circuit, the flow is intended to be unidirectional.

Turning now to FIG. 2, there is shown a crosssectional view of a PEEP valve 12 constructed for use in a breathing circuit of the character identified above, in accordance with this invention. The valve 12 includes a valve housing 46 having an inlet 48 and an outlet 50. It should be pointed out that the terms "inlet" and "outlet" are used herein for convenience in describing the valve 12, however, the gas flow through valve 12, as already noted, is actually bidirectional. The word "inlet" will be used to describe that opening in valve 12 that is connectible to the ventilator 14 (or distensible bag) generally referred to herein as "gas delivery means", and "outlet" will be used to define that opening which is connectible to the remainder of the anesthesia breathing circuit 10. The inlet 48 is shown having a further tubing 52 connected thereto by lock screw 54 and which connects with the ventilator 14 or breathing bag.

Within the valve housing 46 are two parallel paths for the flow of gas. One of the gas flow paths proceeds directly through valve housing 46 through a check valve 56. As shown, the check valve 56 may be the flexible flapper type of rubber or resilient plastic material and is held in position in the gas flow path by a central stub 58 which is press fitted to a web 60 positioned in the gas flow path. The check valve 56 is so positioned such that it freely allows the flow of gas from the inlet 48 to the outlet 50 but prevents reverse flow. The gas, therefore, flows unidirectionally through this gas flow path, always from the ventilator 14 or breathing bag to the remaining portions of breathing circuit 10.

The valve housing 46 also defines another gas flow path which may allow gas to bypass the check valve 56. This path proceeds through inlet 48 and is diverted through opening 62 having a valve seat 64 positioned therein. A flexible diaphragm 66 seats against valve seat 64 to prevent gas flow therethrough and opens when the pressure acting on the underside of diaphragm 66 exceeds a predetermined value. The diaphragm 66 is retained in position at its periphery between a shoulder 68 formed in the valve housing 46 and a washer 70, which is held by an upper housing 72', joined to the valve housing 46 and sealed thereagainst. As shown, the flexible diaphragm 66 has a generally flat area 72 which moves into and out of contact with valve seat 64 to open and close the same, and a curved area 74 which joins the flat area 72 to define an inverted frustum. The periphery of the diaphragm at the frustum base is held against the valve housing 46 as described above.

The flexible diaphragm 66 is thickened along the frustum or cone-shaped portion 76 to form an inward annular projection 78. As the diaphragm 66 is raised, thereby lifting the flat area 72 from valve seat 64, the inward annular projection 78 butts against a downwardly projecting stop 80 formed in the washer 70 by recess 82 and further upward movement of the diaphragm 66 is prevented.

The diaphragm 66 is adjustably spring biased toward its closed position by a spring 84 which has its lower end 86 acting against the flat area 72 of diaphragm 66. The lower end 86 of spring 84 is held in position by spring guide 88 which is fitted into position within diaphragm 66 and has an upwardly facing button 90 which locates and retains the lower end 86 of spring 84 in position.

The upper end 92 of the spring 84 is retained within spring operator 94 which itself is threaded within the upper housing 72' so that the amount of force exerted by the spring bias against the flat area 72 of diaphragm 66 can be adjusted as desired.

THE OPERATION OF THE PEEP VALVE

In the operation of the PEEP valve of the present invention, the valve 12 is located in the breathing circuit 10 as shown in FIG. 1, between the ventilator 14 (or breathing bag) and the remaining parts of the circuit 10. As the ventilator 14 operates in the inhalation mode and the bellows 28 is collapsing to force gas to the patient, the initial flow of gas passes through the check valve 56, FIG. 2, of the valve 12 to the breathing circuit 10 and then to the patient. As the continued collapse of the bellows 28 raises the internal pressure within circuit 10, a predetermined pressure is reached which overcomes the preset spring bias of spring 84, causing the flexible diaphragm 66 to lift from seat 64. Further gas then passes in a parallel flow path to the flow through the check valve 56 to the patient. The diaphragm 66 thereafter remains open until the end of the inhalation mode, at which time, the respirator 14 is shifted to the exhalation mode and the patient is exhaling into the circuit 10. Since the pressure within the breathing circuit 10 has not yet dropped, the initial exhalation gases pass back through the diaphragm valve and into the ventilator bellows 28. The return flow cannot, of course, pass through the check valve 56 of the PEEP valve 12. As the pressure during exhalation is gradually decreased, a predetermined pressure is reached wherein the spring bias of spring 84 overcomes the force of the pressure acting on the diaphragm 66, causing the diaphragm to drop into engagement with valve seat 64, thereby closing completely that flow path to the bellows 28. Since the remaining portions of the breathing circuit 10 are essentially closed, the pressure at which the diaphragm valve closes is maintained in the circuit 10 and acts as the minimum pressure which the lungs can reach during exhalation, thereby establishing a positive end expiratory pressure. The PEEP can, obviously, be changed for different patients by adjusting the spring bias acting against the diaphragm 66.

Any fresh gas added to the circuit 10 during the exhalation, i.e. when the diaphragm valve is closed, acts to raise the pressure within the circuit 10 sufficiently to open the diaphragm valve, thereby allowing that additional flow to pass into the ventilator 14 where it is released to atmosphere since the ventilator 14 is conventionally open to the atmosphere at the end of the exhalation phase. Thus, the pressure within the circuit 10 is not raised by the addition of fresh gases but the preset PEEP is maintained. If a breathing bag is being utilized, instead of a ventilator, the excess flow could be vented to atmosphere by way of a standard Georgia valve, similar to that shown and described in U.S. Pat. No. 3,276,446.

As it will be seen, when the exhalation phase is terminated and the ventilator 14 is again switched to inhalation phase, the cycle will repeat itself, i.e. the initial gas flow will proceed through the check valve 56, gradually increasing in pressure until the diaphragm valve also opens.

Accordingly, by providing a valve of the described design and located between the ventilator 14 (or breathing bag) and the rest of the patient breathing circuit 10, the valve allows establishing a PEEP in the patient's lungs without introducing any significant increased resistance to the patient's exhalation. The diaphragm valve, open, does not offer such resistance and closes fairly rapidly when the circuit pressure has been reduced to the desired minimum PEEP valve, yet, the precise PEEP can be readily adjusted within a desired range of values.

While the present invention has been particularly set forth in terms of specific embodiments thereof, it will be understood in view of the instant disclosure, that numerous variations upon the invention are now enabled to those skilled in the art, which variations yet reside within the scope of the instant teaching. Accordingly, the invention is to be broadly construed, and limited only by the scope and spirit of the claims now appended hereto.

I claim:

1. In a patient breathing circuit having gas delivery means for forcing inhalation anesthesia gas to, and receiving exhalation gas from the patient, the improvement comprising a valve that is connected between said gas delivery means and the remainder of the breathing circuit for retaining positive residual pressure in the breathing circuit at the end of patient exhalation, said valve comprising a housing having an inlet for connection to said gas delivery means, and an outlet for connection to the remainder of the breathing circuit, said inlet and outlet being interconnected within the housing by first and second parallel gas flow paths, a check valve in said first gas flow path adapted to pass gas only in a direction from said gas delivery means into the breathing circuit during patient inhalation, and a pressure operated valve in said second gas flow path that is opened in response to delivered gas pressure during inhalation and is spring-biased to close when the pressure within the second gas flow path drops below a predetermined minimum value of positive pressure during patient exhalation.

2. A breathing circuit valve as defined in claim 1 wherein said pressure operated valve comprises a valve seat and a flexible diaphragm subject to both predetermined forced inhalation pressure and to patient exhalation pressure to cause movement from said seat and opening of said second gas flow path.

3. A breathing circuit valve as defined in claim 2 wherein said flexible diaphragm is in the form of an inverted frustum and has seated therein a spring that is adjustable to set the predetermined minimum value of pressure operable to maintain open said pressure operated valve.

4. A breathing circuit valve as defined in claim 3, wherein stop means in the valve housing are aligned to be engaged by the frustum base to limit the opening movement of said diaphragm above said valve seat.

5. A breathing circuit valve as defined in claim 1, wherein the check valve constitutes a disc that is flexible at its periphery for low resistance to gas flow from the gas delivery means and is fixed at its center with respect to the valve housing.

6. A breathing circuit valve as defined in claim 1, wherein the check valve and pressure operated valve both are opened under gas delivery pressure to admit gas to the breathing circuit during forced inhalation, and the check valve is closed by exhalation pressure and the pressure operated valve is held open by exhalation pressure until it drops below the predetermined minimum pressure setting.

* * * * *